US012796926B2

(12) United States Patent
Wiedeback et al.

(10) Patent No.: US 12,796,926 B2
(45) Date of Patent: *Nov. 17, 2026

(54) SHARING CONTINUOUS GLUCOSE DATA AND REPORTS

(71) Applicant: Dexcom, Inc., San Diego, CA (US)

(72) Inventors: Daniel Justin Wiedeback, Portland, OR (US); Shane Philip Delmore, Portland, OR (US); Jeremy Crawford Sloan, Portland, OR (US); Justin E. Schumacher, Portland, OR (US)

(73) Assignee: Dexcom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/031,150

(22) Filed: Jan. 17, 2025

(65) Prior Publication Data

US 2025/0160642 A1 May 22, 2025

Related U.S. Application Data

(63) Continuation of application No. 17/234,584, filed on Apr. 19, 2021, now Pat. No. 12,232,841, which is a (Continued)

(51) Int. Cl.

*A61B 5/00* (2006.01)
*A61B 5/145* (2006.01)

(Continued)

(52) U.S. Cl.

CPC ............ *A61B 5/0004* (2013.01); *A61B 5/002* (2013.01); *A61B 5/0022* (2013.01);

(Continued)

(58) Field of Classification Search

CPC ..... A61B 5/0004; A61B 5/002; A61B 5/0022; A61B 5/14532; G16H 10/60; G16H 15/00;

(Continued)

(56) References Cited

U.S. PATENT DOCUMENTS 10,453,573 B2 * 10/2019 Greene .................. G16H 40/63
12,232,841 B2 2/2025 Wiedeback et al.

(Continued)

FOREIGN PATENT DOCUMENTS

AU 2016346772 B2 3/2019
AU 2021236556 B2 6/2023

(Continued)

OTHER PUBLICATIONS

Google, "How to Share," Sep. 15, 2014, 3 pages.

(Continued)

*Primary Examiner* — Michael S McNally

(74) *Attorney, Agent, or Firm* — Patterson + Sheridan, LLP

(57) ABSTRACT

In some example embodiments, there is provided a method, which includes sending a message to a server, wherein the message includes a request for a share code to enable another user to access, via a first computer, analyte data obtained from a host-patient associated with a receiver and/or an analyte report for the host-patient associated with the receiver; receiving, in response to the sending, the share code generated by the server, wherein the share code comprises a checksum portion, a password portion, and an identifier portion indicative of the host-patient; generating a user interface view including the share code; and displaying the user interface view including the share code, wherein the share code enables the other user to access, via the first computer, the analyte data and/or the analyte report. Related systems, methods, and articles of manufacture are also disclosed.

20 Claims, 9 Drawing Sheets

Related U.S. Application Data continuation of application No. 15/275,243, filed on Sep. 23, 2016, now abandoned, which is a continuation of application No. 15/274,735, filed on Sep. 23, 2016, now abandoned.

(60) Provisional application No. 62/247,040, filed on Oct. 27, 2015.

(51) Int. Cl.

| | |
|---|---|
| ***G06F 21/60*** | (2013.01) |
| ***G06F 21/62*** | (2013.01) |
| ***G16H 10/60*** | (2018.01) |
| ***G16H 15/00*** | (2018.01) |
| ***G16H 40/63*** | (2018.01) |
| ***H04L 9/40*** | (2022.01) |
| *H04L 67/01* | (2022.01) |
| *H04L 67/06* | (2022.01) |
| *H04L 67/12* | (2022.01) |

(52) U.S. Cl.

CPC ........ *A61B 5/14532* (2013.01); *G06F 21/602* (2013.01); *G06F 21/6245* (2013.01); *G06F 21/6254* (2013.01); *G16H 10/60* (2018.01); *G16H 15/00* (2018.01); *G16H 40/63* (2018.01); *H04L 63/083* (2013.01); *H04L 63/10* (2013.01); *H04L 67/01* (2022.05); *H04L 67/06* (2013.01); *H04L 67/12* (2013.01)

(58) Field of Classification Search

CPC ... G16H 40/63; G06F 21/602; G06F 21/6245; G06F 21/6254; H04L 63/083

USPC .......................................................... 713/165

See application file for complete search history.

(56) References Cited

U.S. PATENT DOCUMENTS

| | | | |
|---|---|---|---|
| 2001/0041831 | A1 | 11/2001 | Starkweather et al. |
| 2002/0193679 | A1 | 12/2002 | Malave et al. |
| 2003/0004403 | A1 | 1/2003 | Drinan et al. |
| 2004/0225878 | A1 | 11/2004 | Costa-Requena et al. |
| 2005/0070778 | A1 | 3/2005 | Lackey et al. |
| 2005/0074126 | A1 | 4/2005 | Stanko |
| 2005/0165623 | A1 | 7/2005 | Landi et al. |
| 2006/0010098 | A1 | 1/2006 | Goodnow et al. |
| 2006/0059016 | A1 | 3/2006 | Ogilvie |
| 2006/0272652 | A1 | 12/2006 | Stocker et al. |
| 2007/0005963 | A1 | 1/2007 | Eldar et al. |
| 2007/0198296 | A1 | 8/2007 | Pellinat et al. |
| 2007/0255946 | A1 | 11/2007 | Kokubun |
| 2009/0198118 | A1 | 8/2009 | Hayter et al. |
| 2009/0242425 | A1 | 10/2009 | Kamath et al. |
| 2010/0257597 | A1 | 10/2010 | Miyazaki |
| 2010/0305965 | A1 | 12/2010 | Benjamin et al. |
| 2011/0173448 | A1 | 7/2011 | Baentsch et al. |
| 2011/0179405 | A1 | 7/2011 | Dicks et al. |
| 2011/0287528 | A1 | 11/2011 | Fern et al. |
| 2012/0232367 | A1 | 9/2012 | Allegri et al. |
| 2012/0242501 | A1 | 9/2012 | Tran et al. |
| 2012/0245447 | A1 | 9/2012 | Karan et al. |
| 2012/0271380 | A1 | 10/2012 | Roberts et al. |
| 2012/0331108 | A1 | 12/2012 | Ferdowsi et al. |
| 2013/0173473 | A1 | 7/2013 | Birtwhistle et al. |
| 2013/0321425 | A1 | 12/2013 | Greene et al. |
| 2014/0012510 | A1 | 1/2014 | Mensinger et al. |
| 2014/0014720 | A1 | 1/2014 | Sarkis, Jr. et al. |
| 2014/0095577 | A1 | 4/2014 | Root et al. |
| 2014/0187890 | A1 | 7/2014 | Mensinger et al. |
| 2015/0070187 | A1 | 3/2015 | Wiesner et al. |
| 2015/0118668 | A1 | 4/2015 | Mayou et al. |
| 2015/0149362 | A1 | 5/2015 | Baum et al. |
| 2015/0205930 | A1 | 7/2015 | Shaanan et al. |
| 2015/0302539 | A1 | 10/2015 | Mazar et al. |
| 2015/0331997 | A1 | 11/2015 | Joao |
| 2015/0363563 | A1 | 12/2015 | Hallwachs |
| 2016/0188799 | A1 | 6/2016 | Borras |
| 2017/0116374 | A1 | 4/2017 | Wiedeback et al. |
| 2017/0116380 | A1 | 4/2017 | Wiedeback et al. |
| 2017/0196472 | A1 | 7/2017 | Felix et al. |
| 2017/0262604 | A1 | 9/2017 | Francois |
| 2021/0020282 | A1* | 1/2021 | Bernstein ............... G16H 10/60 |

FOREIGN PATENT DOCUMENTS

| | | | |
|---|---|---|---|
| WO | 2015066051 | A2 | 5/2015 |
| WO | 2017074623 | A1 | 5/2017 |

OTHER PUBLICATIONS

Hartz T., et al."KernPaeP—a Web-based Pediatric Palliative Documentation System for Home Care," In MIE, 2009, pp. 337-341.
"Upload," Merriam-Webster, Inc. Sep. 6, 2015, 3pages.

* cited by examiner

SHARING CONTINUOUS GLUCOSE DATA AND REPORTS

INCORPORATION BY REFERENCE TO RELATED APPLICATIONS

This application is a continuation of U.S. application Ser. No. 17/234,584, filed Apr. 19, 2021, which is a continuation of U.S. application Ser. No. 15/275,243, filed Sep. 23, 2016, which is a continuation of U.S. application Ser. No. 15/274,735, filed Sep. 23, 2016, which claims the benefit of U.S. Provisional Application No. 62/247,040, filed Oct. 27, 2015. The aforementioned applications are incorporated by reference herein in their entireties, and are hereby expressly made a part of this specification.

TECHNICAL FIELD

The present disclosure generally relates to continuous glucose monitoring.

BACKGROUND

Diabetes mellitus is a disorder in which the pancreas cannot create sufficient insulin. In a diabetic state, a person suffering from high blood sugar may experience an array of physiological side effects associated with the deterioration of small blood vessels. These side effects may include, for example, kidney failure, skin ulcers, bleeding into the vitreous of the eye, and the like. A hypoglycemic reaction, such as a low blood sugar event, may be induced by an inadvertent overdose of insulin, or after a normal dose of insulin or glucose-lowering agent. In a severe hypoglycemic reaction, there may be a high risk for headache, seizure, loss of consciousness, and coma.

A diabetic person may carry a self-monitoring blood glucose (SMBG) monitor which typically requires the user to prick his or her finger to measure his or her glucose levels. Given the inconvenience associated with traditional finger pricking methods, it is unlikely that a diabetic will take a timely SMBG measurement and, consequently, may be unaware whether his or her blood glucose value is indicative of a dangerous situation.

Consequently, a variety of non-invasive, transdermal (e.g., transcutaneous) and/or implantable electrochemical sensors have been and are being developed for detecting and/or quantifying glucose values from such sensor measurements having accuracy corresponding to direct blood glucose measurements. These devices generally transmit raw or minimally processed data for subsequent analysis at a remote device. The remote device may have a display that presents information to a user hosting the sensor. In some systems, a patient may check his or her glucose level on a hand held computing device. There are challenges to presenting this information discreetly and reliably. Moreover, there are challenges to efficiently analyzing this information to provide reports and insights to the diabetic user and his/her caregiver network for managing the diabetic condition.

SUMMARY

Methods and apparatus, including computer program products, are provided for sharing data and/or reports. In some example embodiments, there is provided a method, which includes sending a message to a server, wherein the message includes a request for a share code to enable another user to access, via a first computer, analyte data obtained from a host-patient associated with a receiver and/or an analyte report for the host-patient associated with the receiver; receiving, in response to the sending, the share code generated by the server, wherein the share code comprises a checksum portion, a password portion, and an identifier portion indicative of the host-patient; generating a user interface view including the share code; and displaying the user interface view including the share code, wherein the share code enables the other user to access, via the first computer, the analyte data and/or the analyte report.

In some example embodiments, one of more variations may be made as well as described in the detailed description below and/or as described in the following features. The first computer including an application may provide the share code to the server. The application may comprise a downloaded application and/or a browser that accesses, via a wired connection and/or wireless connection, the server. The providing of the share code may comprise at least one of: entering the share code at a webpage generated by the server; or sending to the server another message including the share code. The server may check the share code to determine whether an account associated with the host-patient indicates that the share code authorizes report generation at the first computer. The checking may further include checking the checksum portion of the share code, checking the password portion of the share code, when the checksum is valid, and verifying the identity portion of the share code by checking whether the identity portion maps to the account associated with the host-patient, when the checksum and password portion are valid. The verifying may further include determining whether a lifetime for the share code has expired. The lifetime may be selected by the host-patient and/or configured as a default time. The server may generate the analyte report, when the checking determines that report generation is authorized for presentation at the first computer. The sending of the request for the share code may be triggered, when the host-patient accesses a share code request icon presented on webpage generated by the server. The third sharing mode may include enabling the other user to access, via the first computer, the analyte data obtained from host-patient associated with the receiver and/or the analyte report for the host-patient associated with the receiver.

When in a first sharing mode, analyte data obtained from the host-patient may be uploaded to the server, wherein the analyte data may include continuous glucose sensor data and patient identifying information identifying host-patient. The uploading to the server may include transmitting the analyte data via at least one of a wired link, a cellular data link, a wireless local area network link, and/or a Bluetooth link. The uploading may be performed by the receiver configured to wirelessly receive at least the continuous glucose sensor data from a continuous glucose sensor affixed to the host-patient. The uploading may be via a remote computer. The uploading may be triggered when the receiver couples via at a wired connection and/or a wireless connection to the remote computer that is authenticated by the server. The authentication may include a login to an account associated with the host-patient. The analyte report may be generated for presentation at the remote computer, wherein the analyte report may include the analyte data and patient identifying information identifying the host-patient.

The analyte data obtained from the host-patient may be uploaded to the server, when in a second sharing mode, wherein the analyte data includes continuous glucose sensor data and excludes patient identifying information identifying the host-patient. The receiver may exclude the patient identifying information by at least one of removing, masking, or encrypting the patient identifying information. The uploading may include transmitting, by the receiver, the analyte data via at least one of a wired link, a cellular data link, a wireless local area network link, and/or a Bluetooth link. The receiver may wirelessly receive the analyte data from a continuous glucose sensor affixed to the host-patient. The uploading may be via the first computer comprising a transient computer, wherein the transient computer is not logged into an account associated with host-patient. The uploading may be triggered by at least one of: coupling the receiver via at a wired connection and/or wireless connection to the transient computer; and receiving an indication of a selection of an icon on a webpage, wherein the icon represents the second sharing mode, wherein the second sharing mode enables another user to access the analyte data obtained from the host-patient associated with the receiver and/or the analyte report for the host-patient associated with the receiver, wherein the second sharing mode inhibits sharing of the patient identifying information identifying the host-patient. When in the second sharing mode, the uploading may be triggered by a second sharing mode upload message sent from the server to the transient computer and/or the receiver. The analyte report may be generated for presentation at the transient computer, when the second sharing mode upload message is received.

In some example embodiments, there may be provided a multimode server. The server may provide a method including generating, by a server, a first report including analyte data obtained from a host-patient associated with a receiver and excluding patient identifying information identifying host-patient, when in a first sharing mode; generating, by a server, a second report including the analyte data obtained from the host-patient associated with the receiver and including patient identifying information identifying the host-patient, when in a second sharing mode; and generating, by a server during a specified lifetime, a third report including the analyte data obtained from the host-patient associated with the receiver, when in a third sharing mode.

In some example embodiments, one of more variations may be made as well as described in the detailed description below and/or as described in the following features. The first sharing mode may further include triggering a data upload to the server to include the analyte data and exclude the patient identifying information identifying the host-patient. The first sharing mode may be triggered when the receiver providing the data is not registered with the server. The first sharing mode may be triggered when the receiver providing the data is not logged in and/or authenticated by the server. The second sharing mode may include triggering a data upload to the server to include the analyte data and include the patient identifying information identifying the host-patient. The second sharing mode may be triggered when the receiver providing the data is registered with the server. The second sharing mode may be triggered when the receiver providing the data is not logged in and/or authenticated by the server. The third sharing mode may include providing a share code to enable sharing of the generated report during the specified lifetime. The share code may include a checksum portion, a password portion, and an identifier portion indicative of the host-patient. The third sharing mode may be triggered when a share code is received at the server. The method may include sending at least one of the first report, the second report, and/or the third report. The server may send to the receiver an indication regarding whether to include or exclude the patient identifying information.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated herein and constitute a part of this specification, show certain aspects of the subject matter disclosed herein and, together with the description, help explain some of the principles associated with the subject matter disclosed herein.

Figure 1:
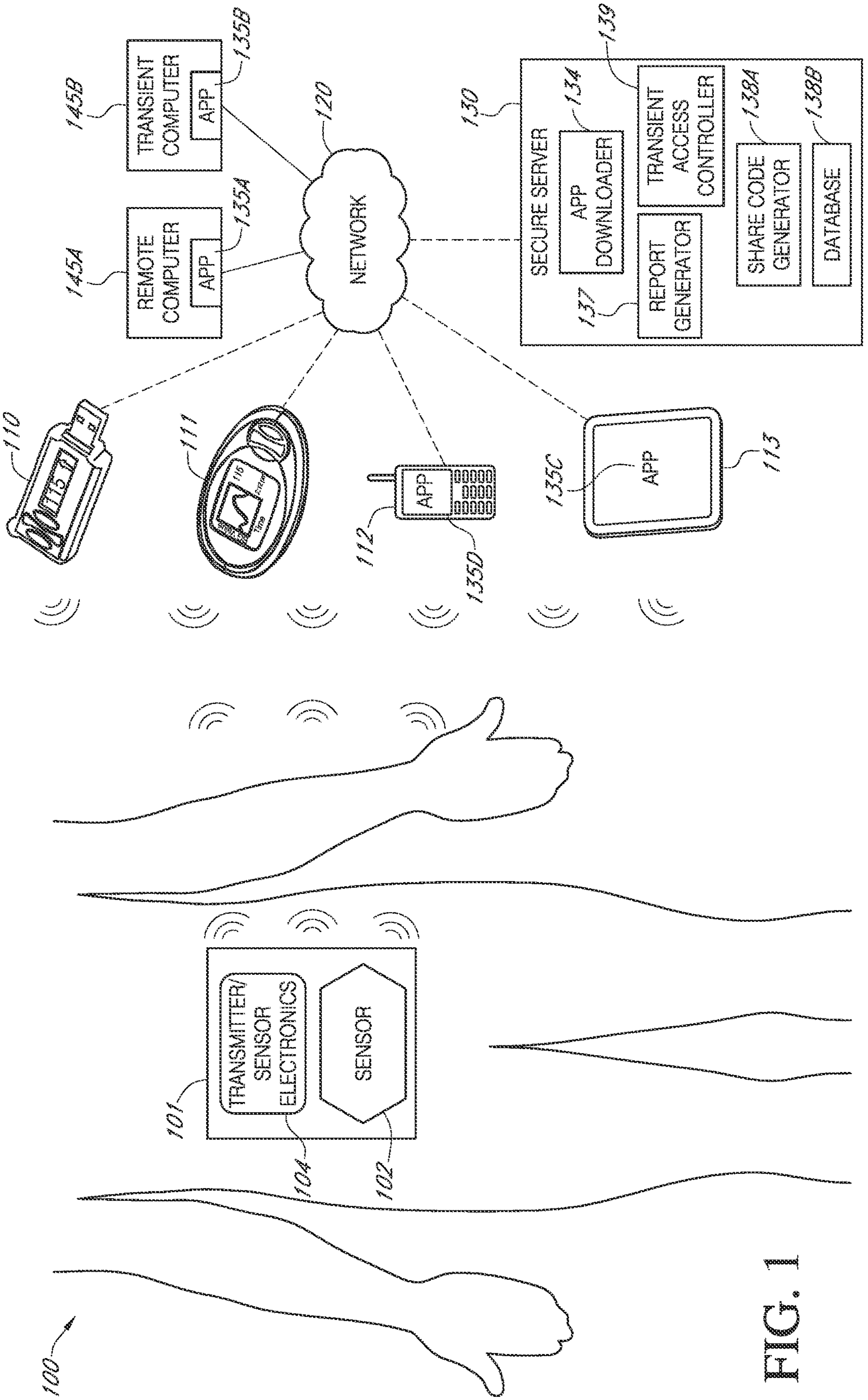
FIG. 1 illustrates a continuous analyte sensor system, in accordance with some example embodiments.

Like labels are used to refer to same or similar items in the drawings.

DETAILED DESCRIPTION

When a patient ("host") is monitored by a continuous glucose monitoring system, the patient may decide to generate reports in real-time as the data is generated by the CGM sensor, or upload the data to a server, such as a secure server, to enable dynamic report generation using historical CGM data as well as other types of data. These reports may provide insights with respect to glucose trends, such as patterns related to low glucose levels, patterns related to high glucose levels, percentage of time within a desired glucose range and/or at a desired glucose level (or, conversely, out of the desired glucose range or not at the desired glucose level, e.g., a percentage of time in a high glucose range or level that is above a certain threshold and/or a percentage of time in a low glucose range or level that is below a certain threshold), and other statistics and information as well. These reports may also take into account other types of data, such as a patient's activity level (for example, calories burned, heartrate, time awake, time sleeping, and the like as measured by a wearable device), diet (for example, caloric intake), treatment activity (for example, medicament dosing, type and/or quantity of medicament, etc.), and the like. As such, these reports may have a meaningful impact with respect to the management of the patient's glucose level. Given the value of this report information, a patient may want to share this information with others, such as caregivers including family, healthcare providers including doctors, nurses, and others. However, the patient should not have to compromise his or her privacy in order to share this information.

In some example embodiments, a CGM receiver may have multiple, configurable sharing modes.

In some example embodiments, the CGM receiver may have at least a first sharing mode, a second sharing mode, and a third sharing mode.

In a first sharing mode, the CGM receiver may couple to a remote computer. This remote computer may include an application, such as a CGM application. The CGM application may comprise an application downloaded from a server, such as a secure server or website for example. Alternatively or additionally, the CGM application may comprise a browser that provides a web interface to a server or secure server. Moreover, the remote computer may be registered with, or logged in to, the secure server, so that the secure server can detect the remote computer's provenance (for example, trust level) as being affiliated with the patient (for example, via a login, an IP address, a MAC address, and/or the like). Although the previous example describes the CGM application as being downloaded from a server, this application may be provided to the remote computer in other ways as well.

When the patient logs in to the secure server via the remote computer including the CGM application, the remote computer may upload, from the CGM receiver, CGM data and forward the uploaded data from the CGM receiver to the secure server, where the patient's CGM data may be stored and used to generate reports.

In some example embodiments, the remote computer including the CGM application may, while logged in to the secure server for example, receive the host patient's CGM data, alerts, and the like and receive the host patient's CGM report(s) generated by the secure server. In this way, the patient can view their CGM reports on the remote computer. In some example embodiments, the remote computer is allowed to receive the CGM data, alerts, and reports so long as the CGM receiver is coupled to the remote computer via a wired or wireless link.

Although the first sharing mode is useful, this first sharing mode represents a trusted mode as the CGM reports are presented with information identifying the patient, so the first sharing mode may not always be appropriate for sharing with others. For example, the remote computer may be a home computer, so sharing patient identifying information on this computer may not represent a security or privacy risk. In contrast, if the computer is a public or semi-public computer used by a variety of people, such as a shared computer at a clinic or doctor's office for example, the first sharing mode may not suitable with respect to security and privacy given the so-called "transient" nature of the computer. As such, the CGM receiver may operate in the second or third sharing modes to provide some level of privacy when sharing CGM data including reports.

In the second sharing mode, the CGM receiver may couple to a transient computer. For example, a patient may visit a clinic or a hospital, and then couple, via a wired or wireless link, to the transient computer. This computer may include a CGM application that can provide access, such as browse, to the secure server or a web page affiliated with the secure server. When in the second sharing mode, the CGM receiver may upload data to the secure server via the transient computer. However, while in the second mode, the CGM receiver may perform this upload in an anonymous mode. For example, the CGM receiver may upload the patient's CGM data but patient identifying information may not be uploaded via the transient computer to the secure server. For example, the CGM receiver may upload data to the server but remove the patient identifying information. Alternatively or additionally, the CGM receiver may upload data to the secure server but anonymize (for example, scramble or mask with all "1" for example) any patient identifying information. Alternatively or additionally, the CGM receiver may upload data to the server but encrypt the patient identifying information, such as the patient's name, the CGM receiver serial number, and/or other patient identifying information.

In some example embodiments, a CGM receiver may, via a wireless or wired link, couple to a computer, such as a transient computer, to perform a data upload to a server, such as a secure server. When that is the case, the transient computer may access (for example, browse to) a web page associated with the secure server. At this web page, the user may select an anonymous upload mode icon on the web page. This selection may trigger instructions to the CGM receiver and/or transient computer to upload CGM data and/or other data from the CGM receiver without patient identifying information. Once the data is uploaded to the secure server, the secure server may generate reports, which can be presented at the computer, for example. But the reports may be generated and presented at the transient computer without patient identifying information.

Although the previous example describes a user of the CGM receiver selecting via a web page the second, anonymous upload mode, this second mode may be triggered in other ways as well. For example, the secure server may assess the provenance of the uploading, transient computer, for example, whether the uploading, transient computer is on a trusted computer list for the CGM receiver, whether the access is logged in to a patient's account, whether the IP or MAC address is associated with the patient's account, and/or the like. Based on this assessment, the secure server may send an anonymous upload mode message to the transient computer and/or CGM receiver to trigger the anonymous upload mode. Alternatively or additionally, the CGM receiver may detect the provenance of the transient computer, and configure the anonymous upload mode accordingly.

To view reports in the second sharing mode, the transient computer including the CGM application may present CGM reports generated by the secure server. However, the CGM reports generated for the second sharing mode may be anonymized, so that the reports do not show patient identifying information, such as the patient's name, the CGM receiver serial number, and other patient identifying information. Moreover, the transient computer including the CGM application may be configured to not store or email reports, so that after the session the CGM reports presented by transient computer including the CGM application may not be persisted to permanent storage. In this way, the patient can view their CGM reports with a caregiver in a relatively secure manner, while the CGM receiver is coupled to the transient computer and in the second sharing mode.

In the third sharing mode, the patient may provide a share code to another user, such as a caregiver and the like. For example, the patient may access the secure server via the CGM receiver or a computer, such as a remote computer. Next, the patient may select, via a user interface view presented at the CGM receiver or computer, share code generation. This selection may trigger a request for the share code to be generated. This request may also specify a time over which the share code is valid. The secure server may then generate a share code and associate the share code with the requesting patient's account. Next, the secure server may provide (for example, transmit, send, and the like) the share code to the CGM receiver or remote computer. The patient may then provide the share code to another user, such as a caregiver. To provide the share code, the patient may email, text, or provide the code in any other way.

With the share code, the caregiver may access, via for example a transient computer, the secure server and request CGM reports for the patients. Moreover, the share code may be valid for a time specified by the patient, as noted. When this is the case, the caregiver may access the secure server to obtain the patient's CGM reports for the duration specified by the selected or configured time. While in the third sharing mode, the transient computer including the CGM application may provide for presentation CGM reports generated by the secure server. However, the secure server may generate CGM reports for a limited time period, which can be selected by the user patient or provided as a default time by the secure server. While in this third, share code mode, the secure server may generate CGM reports including patient identifying information. When this is the case, the CGM receiver uploads CGM data to the secure server including patient identifying information. While in the share code mode, the secure server may be configured to generate CGM reports without patient identifying information as well so that the reports lack patient identifying information, such as a patient's name, the CGM receiver serial number, and/or other patient identifying information. When this is the case, the CGM receiver may upload CGM data to the secure server without patient identifying information.

Moreover, the transient computer including the CGM application may be configured to not store or email reports, so that after the session the CGM reports presented are not persisted to storage. In this way, the third sharing mode allows a patient to provide CGM reports to another user in a relatively secure manner (for example, anonymized and for a limited time period).

Before providing additional details for the three modes, the following provides an example system description in which the multimode system may be implemented.

FIG. 1 is a schematic view of a continuous analyte sensor system 100 coupled to a host, such as a patient, and communicating with a number of example devices 110-113, in accordance with some example embodiments.

A transcutaneous analyte sensor system 100 includes an on-skin sensor assembly 101 that is fastened to the skin of a host via a disposable inserter or applicator (not shown). The system 100 includes a transcutaneous analyte sensor 102 and a transmitter/sensor electronics unit 104 for wirelessly transmitting analyte information to a receiver or receivers, such as devices 110-113. In some alternative embodiments, the sensor may be non-invasive.

During use, a sensing portion of the sensor 102 is under the host's skin, and a contact portion of the sensor 102 is electrically connected to the electronics unit 104. The electronics unit 104 engages a housing of the on-skin assembly 101 (not shown), and the sensor 102 extends through the housing. The housing, which maintains the assembly 101 on the skin and provides for electrical connection of the sensor 102 to sensor electronics provided in the electronics unit 104, is attached to an adhesive patch (not shown) fastened to the skin of the host.

The on-skin sensor assembly 101 may be attached to the host with an applicator (not shown) adapted to provide convenient and secure application. Such an applicator may also be used for attaching the electronics unit 104 to a housing, inserting the sensor 102 through the host's skin, and/or connecting the sensor 102 to the electronics unit 104. Once the electronics unit 104 is engaged with the housing and the sensor 102 has been inserted and is connected to the electronics unit 104, the applicator detaches from the sensor assembly.

The continuous analyte sensor system 100 includes any sensor configuration that provides an output signal indicative of a concentration of an analyte. The output signal, which may be in the form of, for example, sensor data, such as a raw data stream, filtered data, smoothed data, and/or otherwise transformed sensor data, is sent to a receiver, which is described in more detail below. In various embodiments, the analyte sensor system 100 includes a transcutaneous glucose sensor, a subcutaneous glucose sensor, a continuous refillable subcutaneous glucose sensor, or a continuous intravascular glucose sensor, for example.

In some embodiments, the sensor 102 extends through a housing (not shown), which maintains the sensor on the skin and provides for electrical connection of the sensor-to-sensor electronics, provided in the electronics unit 104. In some embodiments, the sensor 102 is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches, albeit other dimensions of the conductive body can be used. A membrane system may be deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface.

The membrane system may include a plurality of domains, for example, an electrode domain, an interference domain, an enzyme domain (for example, including glucose oxidase), and a resistance domain, and can include a high oxygen solubility domain, and/or a bioprotective domain. The membrane system may be deposited on the exposed electroactive surfaces using known thin film techniques (for example, spraying, electro-depositing, dipping, etc.). In some embodiments, one or more domains are deposited by dipping the sensor into a solution and drawing out the sensor at a speed that provides the appropriate domain thickness. However, the membrane system can be disposed over (or deposited on) the electroactive surfaces using any known method.

In the illustrated embodiment, the electronics unit 104 is releasably attachable to the sensor 102, which together form the on-skin sensor assembly 101. The electronics unit 104 includes electronic circuitry associated with measuring and processing the continuous analyte sensor data, and is configured to perform algorithms associated with processing and calibration of the sensor data. The electronics unit 104 may include hardware, firmware, and/or software that enable measurement of levels of the analyte via the analyte sensor 102, e.g., such as glucose levels in embodiments of the analyte sensor 102 as a glucose sensor. For example, the electronics unit 104 can include a potentiostat, a power source for providing power to the sensor 102, other components useful for signal processing and data storage, and preferably a telemetry module for one- or two-way data communication between the electronics unit 104 and one or more receivers, repeaters, and/or display devices, such as the devices 110-113. Sensor electronics within the electronics unit 104 can be affixed to a printed circuit board (PCB), etc., and can take a variety of forms. For example, the electronics can take the form of an integrated circuit (IC), such as an application-specific integrated circuit (ASIC), a microcontroller, and/or a processor. The electronics unit 104 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, such as estimated glucose values (EGVs), and/or the like.

The devices 110-113 may operate as repeaters, receivers, and/or display devices (also referred to herein more generally as "receivers" or "CGM receivers"). In the example of FIG. 1, device 110 comprises a key fob repeater 110, device 111 comprises a dedicated medical device receiver 111, device 112 comprises a smart phone 112 including an application 135D (e.g., such as a CGM application) to provide the receiver disclosed herein, and device 113 comprises a portable or tablet computer 113 including an application 135C (e.g., such as a CGM application) to provide the receiver disclosed herein; although other types of devices capable of receiving, repeating, and/or displaying the analyte sensor data provided by electronics unit 104 may be used as well. Devices 110-113 may be operatively linked (via wireless link(s)) to the electronics unit 104.

The repeaters, receivers, and/or display devices 110-113 may receive data from electronics unit 104, which is also referred to as the transmitter and/or sensor electronics body herein. For example, the sensor data can be transmitted from the sensor electronics unit 104 to one or more of the key fob repeater 110, the medical device receiver 111, the smart phone 112, the portable or tablet computer 113, and the like.

In some implementations, the repeaters, receivers and/or display devices may also transmit data to the electronics unit 104. In some implementations, the repeaters, receivers, and/or display devices may transmit data to one another or to other servers and/or computers. For example, medical device receiver 111 may receive analyte data such as CGM data from transmitter 104. Medical device receiver 111 may display the CGM data as well as related alerts and the like. Medical device receiver 111 may also provide the CGM data to other devices, such devices 110, 112, 113, as well as one or more other servers, such as secure server 130, via for example network 120 and/or directly through wired or wireless communications. Similarly, for example, smart phone 112 may receive the CGM data directly from the transmitter 104. Smart phone 112 can display the CGM data as well as related alerts and the like, as well as may also provide the CGM data to other devices, such as the devices 110, 113, or wearable devices like a smart watch or smart glasses connected to the smart phone 112, as well as one or more other servers, such as secure server 130, via for example network 120 and/or directly through wired or wireless communications.

Data output from an output module of the receiver can provide wired and/or wireless, one- or two-way communication between the receiver and an external computing device. This external computing device can be any device that interfaces or communicates with the receiver. In some embodiments, the external computing device is a computer or server, and the receiver is able to download current and/or historical data for retrospective analysis by a patient, caregiver, physician, and the like for example. In some embodiments, the external computing device is a modem, and the receiver is able to send alerts, warnings, emergency messages, etc., via telecommunication lines to another party, such as a doctor and/or a family member. In some embodiments, the external computing device is an insulin pen or insulin pump, and the receiver is able to communicate therapy recommendations, such as an insulin amount and a time to the insulin pen or insulin pump. The external computing device can include other technology or medical devices, for example pacemakers, implanted analyte sensor patches, other infusion devices, telemetry devices, etc. Moreover, in some example embodiments, a variety of data, such as the therapy recommendations, and other device information, such as fitness monitors, pacemakers, etc., may be uploaded to the secure server in accordance with first, second, and/or third modes disclosed herein. In addition, the reports generated in accordance with first, second, and/or third sharing modes disclosed herein may include a variety of data including therapy recommendations, other device data, etc.

The receiver may communicate with other devices via any suitable communication protocol including radio frequency (RF), Bluetooth, Bluetooth Low Energy (BLE), universal serial bus (USB), any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, 3G, 4G, 5G, LTE, ANT, and/or a proprietary communication protocol.

Remote computer 145A may be accessed by the host-patient or others (when authorized) to access CGM data and/or CGM reports, and the data and reports may be obtained from the devices 111-113 or secure server 130. For example, remote computer 145A may be utilized by the host-patient, a remote follower (such as a parent or the like assisting in the tracking of the host-patient's CGM data), or other user.

In some example embodiments, remote computer 145A may download from a server, such as secure server 130, an application such as CGM application 135A for receiving, transmitting, and/or displaying CGM data as well as other types of data. In some example embodiments, CGM application 135A may also present reports generated by the secure server. Moreover, CGM application 135A may enable a CGM receiver to upload data to secure server 130. While continuous glucose monitoring (CGM) data is discussed in this and other examples in this disclosure, it is understood that other analyte data can be monitored and processed in accordance with the various embodiments of the present technology.

In some example embodiments, CGM application 135A may, alone or in combination with secure server 130, control whether to implement a first sharing mode, second sharing mode, or third sharing mode. In some example embodiments, a web page at the secure server may allow selection of the first sharing mode, second sharing mode, and/or third sharing mode. For example, the CGM application may browse to the web page and select a user interface element corresponding to one of modes. The selection may trigger the CGM application (for example, an uploader at the CGM application) to share data in accordance with the selected mode.

Transient computer 145B may be similar to remote computer 145A in some respects but may be a computer that is not typically used by the host-patient. For example, the transient computer 145B may be a shared computer at a clinic, where the patient may be receiving care. In this example, the patient may want to share CGM data and/or other data with for example a caregiver, such as a nurse or doctor. But the patient may want to limit access to the CGM data and report data in order to enhance privacy, especially in this example where the transient computer is a shared, semi-public computer at clinic. While in the second sharing mode or third sharing mode, the patient's CGM data and CGM reports may be viewed via the CGM application 135B.

The secure server 130 may have at least one processor and at least one memory storage device, such as a database, that receives, stores, and processes data received from one or more of the key fob repeater 110, the medical device receiver 111, the smart phone 112, the portable tablet computer 113, and other devices. A remote device may couple to the server 130 to access sensor data associated with a given host coupled to the sensor/transmitter. For example, a caregiver, a parent, and/or the like at a computer 145A or 145B may receive, from the secure server or other device, sensor data, reports, associated alerts, and the like to remotely follow a host-patient at receiver 112.

Server 130 may comprise one or more servers accessible via a network, such as the Internet and the like. The secure server 130 may be secure in the sense that patient data may be secured in order to restrict access to a patient's private data, such as the patient's CGM data, patient identifiable data, therapy recommendations, other device data, and/or the like. The secure server 130 may include a database 138B for storing analyte data for the host(s) and/or other host related data and for mapping each host account to a share code including options; a share code generator 138A for generating share codes; a report generator 137 for generating CGM reports for one or more patients; a transient access controller 139 for controlling access via the sharing modes disclosed herein; and/or an application downloader 134 for providing a CGM application to example devices, such as computers 145A-B and devices 110-113; and/or one or more web pages where a share mode selection may be performed.

The display device, such as tablet 113, may generate a user interface view, via the CGM application 135C for example, for presentation at a display. This user interface view may include analyte values, such as CGM data, prompts or messages to convey information to the user, such as reference outlier values, requests for reference analyte values, therapy recommendations, deviation of the measured analyte values from the estimated analyte values, CGM reports (for example, reports including CGM-related information for the host-patient), prompts to guide the user through calibration or troubleshooting of the calibration, other device data (for example, fitness data, pacemaker data, infusion pump data, other sensor data, etc.) and/or the like. A device may download the CGM application disclosed herein from server 130, although the CGM application may be configured on the device in other ways as well (for example, pre-configured during manufacture and the like).

Figure 2:
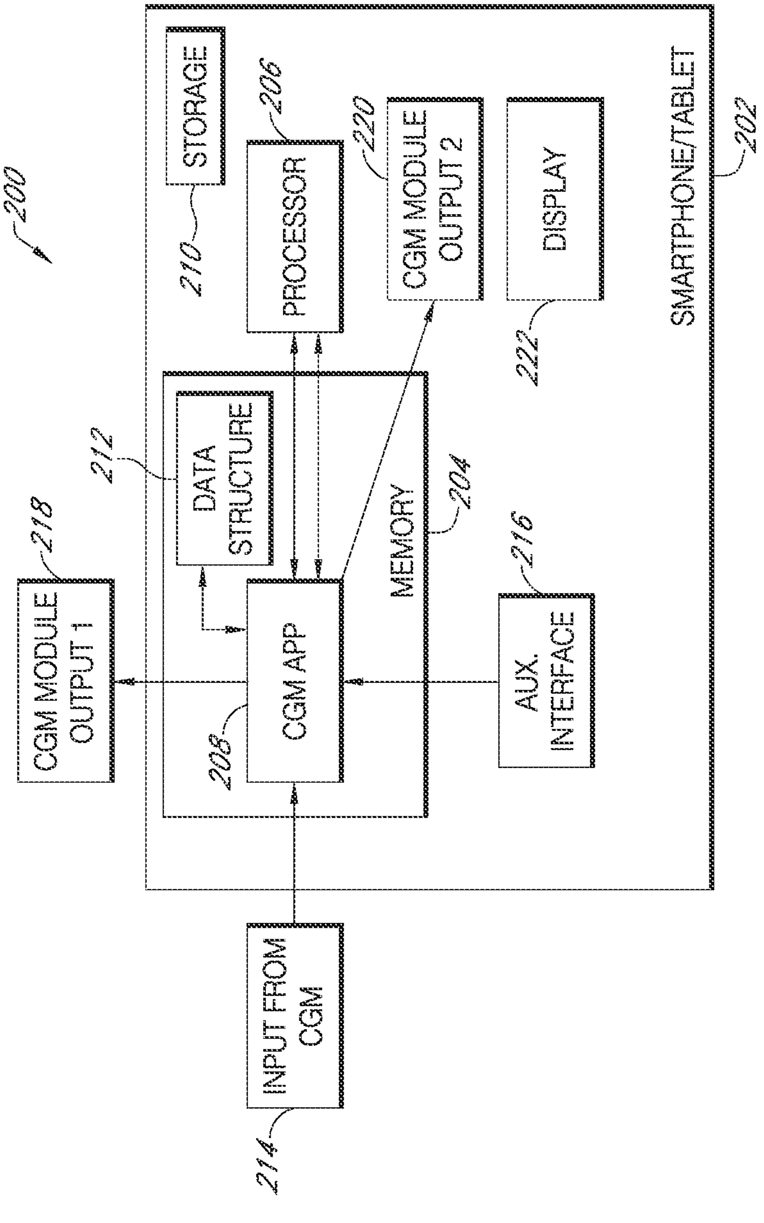
FIG. 2 illustrates a functional block diagram of a mobile device used with the continuous analyte sensor system, in accordance with some example embodiments.

FIG. 2 is a functional block diagram of an embodiment of a system 200 for leveraging mobile device features in continuous analyte monitoring, such as continuous glucose monitoring, according to some example embodiments.

The system 200 may comprise a mobile device 202, which may be any type of computing device capable of receiving one or more inputs and producing an output. Examples of the mobile device 202 include a smart phone 112, a tablet 113 computing device, a laptop, and/or the like. The mobile device 202 may include at least one memory 204 and at least one processor 206. The memory 204 may provide the processor 206 access to data and program information that is stored in the memory 204 at execution time. Typically, the memory 204 may include random access memory (RAM) circuits, read-only memory (ROM), flash memory, etc., or a combination thereof. The processor 206 may be, or may include, one or more programmable general-purpose or special-purpose microprocessors 206, digital signal processors 206 (DSPs), programmable controllers, application specific integrated circuits (ASICs), programmable logic devices (PLDs), etc., or a combination of such hardware-based devices.

In accordance with some embodiments, the processor 206 may execute a continuous glucose monitoring (CGM) application 208 out of the memory 204.

In accordance with some embodiments, CGM application 208 may be configured to control, alone or in combination, the multiple sharing modes disclosed herein. Moreover, the CGM application may be configured to receive data from the transmitter, display CGM data, alerts, messages, and reports (for example, which may be generated by the secure server or generated at the CGM application itself), transmit (or upload) data to other devices, such as server 130, computers 145A-B, and devices 110-113, and receive data from other devices, such as server 130, computers 145A-B, and devices 110-113. The CGM application may, as noted, comprise a browser configured to access via network 120 (for example, the Internet) the secure server. The CGM application may also be configured to analyze CGM data provided by a transmitter as well as other data provided by other devices. As used herein, the phrase or term associated with the CGM application should be construed broadly to include not just the application itself, but also integration with sensor 102, other diabetes management devices, including insulin delivery therapies such as insulin pumps, insulin pens, or other drugs useful for the treatment of diabetes. In other words, the CGM application may perform other functions besides monitoring glucose (which may include interstitial and/or blood glucose measurements). It could, for example, determine that a user's glucose level is high, and then transmit a signal to the user's insulin pump to administer a quantity of insulin to bring the user's glucose level down.

A software and/or firmware component of the CGM application 208 may be stored in storage 210 available to the mobile device 202, and loaded into the memory 204 at execution time. The storage 210 may be any non-transitory computer readable media including, but not limited to, a hard disk, EEPROM (electrically erasable programmable read only memory), a memory stick, or any other storage device type. The memory 204 may contain one or more data structures 212 that the CGM application 208 accesses during execution. For example, the CGM application 208 may receive an input and store the input as an input parameter in a data structure 212 in the memory 204 for later processing.

In some embodiments, the CGM application 208 may be embodied as downloadable software that a user may download from a remote server, such as server 130, through a wired or wireless connection. For example, the user may access the server using an application already installed on the user's mobile device. The user may then download and install the CGM application 208 with the aid of the application. The user may then configure the CGM application 208. For example, the configuration may include setting the user's personal preferences and/or settings, such as contacts, events, modes, profiles, and/or the like. The configuration may be done manually, such as by selecting various options from menus, or automatically. In automatic configuration, the CGM application 208 reads the user's preferences and/or settings that are stored on the mobile device 202. For example, in some implementations, the CGM application 208 would first discover what other applications are installed on the mobile device, and then access those applications' data stored in the mobile device's storage and/or remote storage accessible by the mobile device 202 to initially populate the CGM application 208 during set up.

In some implementations of the system 200, the CGM application 208 operating on the mobile device 202 receives at least one input 214 from the CGM transmitter or other device, such as devices 110-113. For example, the input can include a current estimated glucose value (EGV) for the patient or user input by and/or about the patient. In some implementations, the CGM application 208 receives input from an auxiliary interface 216. The auxiliary interface 216 may be any of hardware, software, firmware, or a combination of any of these, and may comprise anything that may be combined with EGV data and processed to produce an output that can provide the user with information that can help him or her make more informed decisions about how to manage his or her glucose. In some embodiments, for example, the auxiliary interface 216 may be a sensor, which may be internal or external to the mobile device 202, or may be another application executed by the mobile device 202.

In some implementations of the system 200, the CGM application 208 operating on the mobile device 202 processes the inputs in conjunction with the processor 206 to produce one or more outputs 218, 220. For example, the output 218 may be to a device or receiver external to the mobile device 202 (shown as CGM Module Output 1, 218, in FIG. 2), or to a device internal to the mobile device 202 (shown CGM Module Output 2, 220), such as to a display 222 or storage 210.

Figure 3:
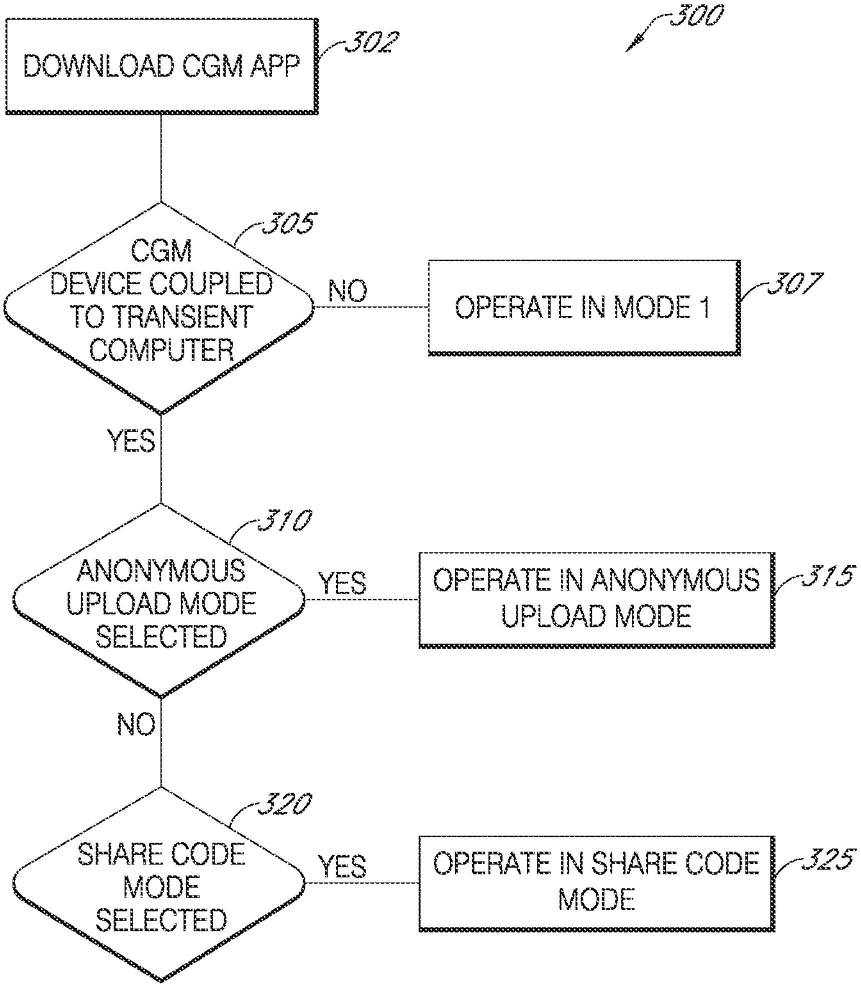
FIG. 3 illustrates an example of a process for providing multiple sharing, in accordance with some example embodiments.

FIG. 3 illustrates a process 300 flow illustrating the multiple modes of operation for system 100, in accordance with some example embodiments.

At 302, a CGM application may be downloaded to a device, in accordance with some example embodiments. For example, server 130 may download one or more CGM applications 135A-D to one or more devices, such as a remote computer 145A, transient computer 145B, other devices 110-113, and/or the like. The CGM application may be downloaded on demand when requested for example, although the CGM application may be installed and/or configured at other times as well (for example, during the manufacture of the device). Moreover, the downloaded CGM application may be updated by the secure server 130 from time to time to provide software updates and the like.

To illustrate further, smart phone 112 may, in addition to providing cellular and internet function, may download CGM application 135D. This smart phone 112 may couple to a computer, such as a remote computer 145A (although other types of computers may be coupled to as well). The computer 145A may be a computer that is associated with the host patient's device. For example, the smart phone 112 (which in this example provides a CGM receiver) including CGM application 135D may be coupled via a wired link for example, such as a USB link, to the remote computer 145A, which may also including a corresponding CGM application 135A (although the link may be wireless as well). The CGM application 135A may be registered to or associated with the host patient of the CGM receiver. For example, the remote computer 145A may be the host patient's home computer, and, as such, there may be a higher degree of trust (or known provenance, for example) when compared to other computers. Alternatively or additionally, remote computer 145A may be associated with a caretaker (for example, a parent and the like) of the host patient, and, as such, there may be a higher degree of trust (or known provenance, for example) when compared to other computers. In both of these examples, the computers are not transient computers, but rather the computers that are somewhat private computers used primarily by the host patient or a remote follower (for example, a person authorized to follow the host patient having a computer of relatively known provenance). Moreover, the remote computer 145A may from time to time access a web page at the secure server, and, as such, the secure server may further detect the provenance of the remote computer (for example, via login(s), IP addresses, MAC addresses, and/or the like). By contrast, a transient computer may be characterized as a computer that is publicly accessible by users other than the host patient or remote follower. For example, a transient computer 145B may be a shared computer at a clinic where a variety of patients and caregivers that may seek access to CGM data and corresponding CGM reports. As such, the transient computer 145B may not be trusted and, as such, the transient computer may not be trusted or the provenance of the transient computer (for example, via prior login(s) and/or the like) may not be detected or known.

If the computer (to which the CGM couples) is not a transient computer (no at 305 to arrive at block 307), the sharing mode may be configured to operate in a first sharing mode. In the first sharing mode, the CGM receiver with CGM application 135C-D, for example, may couple to the remote computer 145A to gain access to the remote computer 145A and/or the secure server 130. The remote computer 145A may be registered with, or logged in to, the secure server 130, so that the secure server recognizes the remote computer as being affiliated with the patient and the patient's device (for example, via login to the user's account, an IP address, a MAC address, login credentials, and the like). After a login for example, remote computer 145A may upload CGM data from the CGM receiver to the secure server to enable storage and report generation. Moreover, the remote computer and/or CGM receiver may receive CGM reports and other data generated by the secure server. While in the first sharing mode, the CGM data, reports, and the like may include patient identifying information since there is a certain degree of trust with respect to the remote computer 145A. The first sharing mode may be selected at a web page presented at the remote computer 145A or the CGM receiver (for example, at CGM application 135D on smart phone 112). Alternatively or additionally, the first sharing mode may be implemented automatically, without user selection. For example, the secure server 130 and/or CGM application 135D on the smart phone 112 may detect that the user of smart phone 112 and CGM application 135D has logged in to the host patient's account, and that data can be uploaded and/or reports presented in accordance with the first mode.

If the computer (to which the CGM receiver couples to) is a transient computer, the host patient may be asked to select whether the sharing mode should be the second sharing mode (labeled "anonymous upload mode"), in accordance with some example embodiments (yes at 305 and 310). For example, the user may be presented with a user interface view indicating whether the second sharing mode should be implemented. When this is the case, the host patient may select the second sharing mode to enable the anonymous upload and sharing in accordance with the second sharing mode (yes at 310 to arrive at block 315).

Although the previous example refers to the selection of the second sharing mode by a user at a user interface, the second mode may be selected in other ways. For example, the second mode may be triggered by a message from the secure server. Alternatively or additionally, the second sharing mode may be a default mode configured during the provisioning of the CGM receiver, for example. Alternatively or additionally, the second sharing mode may be selected programmatically based on a scan of the computer to which the CGM receiver is coupled. For example, if a scan reveals that the computer is not on a trusted list of computers or the provenance of the computer is unknown, the CGM receiver and/or secure server may programmatically select the second sharing mode. For example, the secure server 130 and/or CGM receiver (for example, CGM application 135D on smart phone 112) may detect whether the sharing mode should be a second sharing mode. Specifically, the user of the CGM application 135D of smart phone 112 may not be logged in to the secure server 130, when the smart phone 112 couples to the transient computer 145B for an upload. Alternatively or additionally, the secure server 130 may not detect the provenance (and thus trust level) of the transient computer 145B, and thus trigger the second sharing mode. Alternatively or additionally, the secure server may receive a request, such as an email or a web page request, to access the patient's data including CGM data. When this is the case, the secure server may send a message to the CGM receiver (for example, smart phone 112 including CGM application 135D) indicating to the user to select whether the second mode should be selected for use.

At 315, the CGM receiver may upload data to the secure server via the transient computer, but in the second sharing mode, the CGM receiver may perform this upload in an anonymous mode. For example, the CGM receiver (for example, smart phone 112 configured with CGM application 135D) may upload the patient's CGM data not provide the patient identifying information as noted above. To view reports in the second sharing mode, the transient computer 145B including the CGM application 135B may provide for presentation CGM reports generated by the secure server 130. While in the second sharing mode, the CGM reports generated for the second sharing mode may be anonymized so that the reports do not show, as noted, patient identifying information, such as the patient's name, the CGM receiver serial number, and/or other patient identifying information. In some implementations, the transient computer including the CGM application may be configured to not store or send reports (e.g., via email). In this way, the second sharing mode provides some security when a host patient seeks to share CGM data from a CGM receiver or CGM reports generated by the secure server with another, such as a caregiver, using a transient computer. For example, the upload of the CGM data from the CGM receiver (for example, smart phone 112 configured with CGM application 135D) via transient computer 145B to the secure server may be secure, e.g., because the CGM data (as well as any other uploaded data) may be anonymized and thus does not include patient identifying information as noted above. In addition, any reports generated by the secure server 130 and presented at the transient computer 145B are secure, e.g., as the reports do not include the patient identifying information.

If the second sharing mode is not selected at 310 (no at 310), the host patient may select the third sharing mode (labeled "share code mode"), in accordance with some example embodiments. For example, the user of the CGM receiver (for example, smart phone 112 configured with CGM application 135D) may access a web page of the secure server 130. This web page may include an icon, which when selected triggers the third, sharing mode (yes at 320 to arrive at block 325).

Although the previous example refers to the selection of the third sharing mode by a user at a user interface, the third mode may be selected in other ways. For example, the third sharing mode may be triggered by a message from the secure server. For example, the secure server may receive a request (for example, an email, SMS message, or web page request or indication) to access the patient's data including CGM data. When this is the case, the secure server may send a message to the CGM receiver (for example, smart phone 112 including CGM application 135D) indicating to the user to select whether the third mode should be selected for use. Alternatively or additionally, the secure server 130 may not recognize the provenance of a computer requesting access to the user's data, and, as such, send a message to smart phone 112 including CGM application 135D indicating (or requesting) the third sharing mode. Alternatively or additionally, the third sharing mode may be a default mode configured at the CGM receiver, whenever the CGM receiver does not recognize the provenance of the computer to which it couples.

At 325, the host patient may receive a share code, in accordance with some example embodiments. For example, the share code may be generated by the secure server and provided to a computer or the CGM receiver. When the patient has the share code, the patient may provide a share code to another user, such as a caregiver and the like. With the share code, the other user may access, via for example a transient computer, the secure server and request CGM reports for the patients. Moreover, the share code may be valid for a time specified by the patient, so after the expiration of the share code, the transient computer will not be allowed to receive, for that user/patient, CGM reports from the secure server. As noted above, the CGM reports may be presented with patient identifying information, although the CGM reports may be presented without patient identifying information, such as the patient's name, the CGM receiver serial number, and/or other patient identifying information. In addition, the transient computer including the CGM application may be configured to not store or send reports. In this way, the third sharing mode provides some security when a host patient seeks to share CGM data from a CGM receiver or CGM reports generated by the secure server with a caregiver using a transient computer.

Figure 4A:
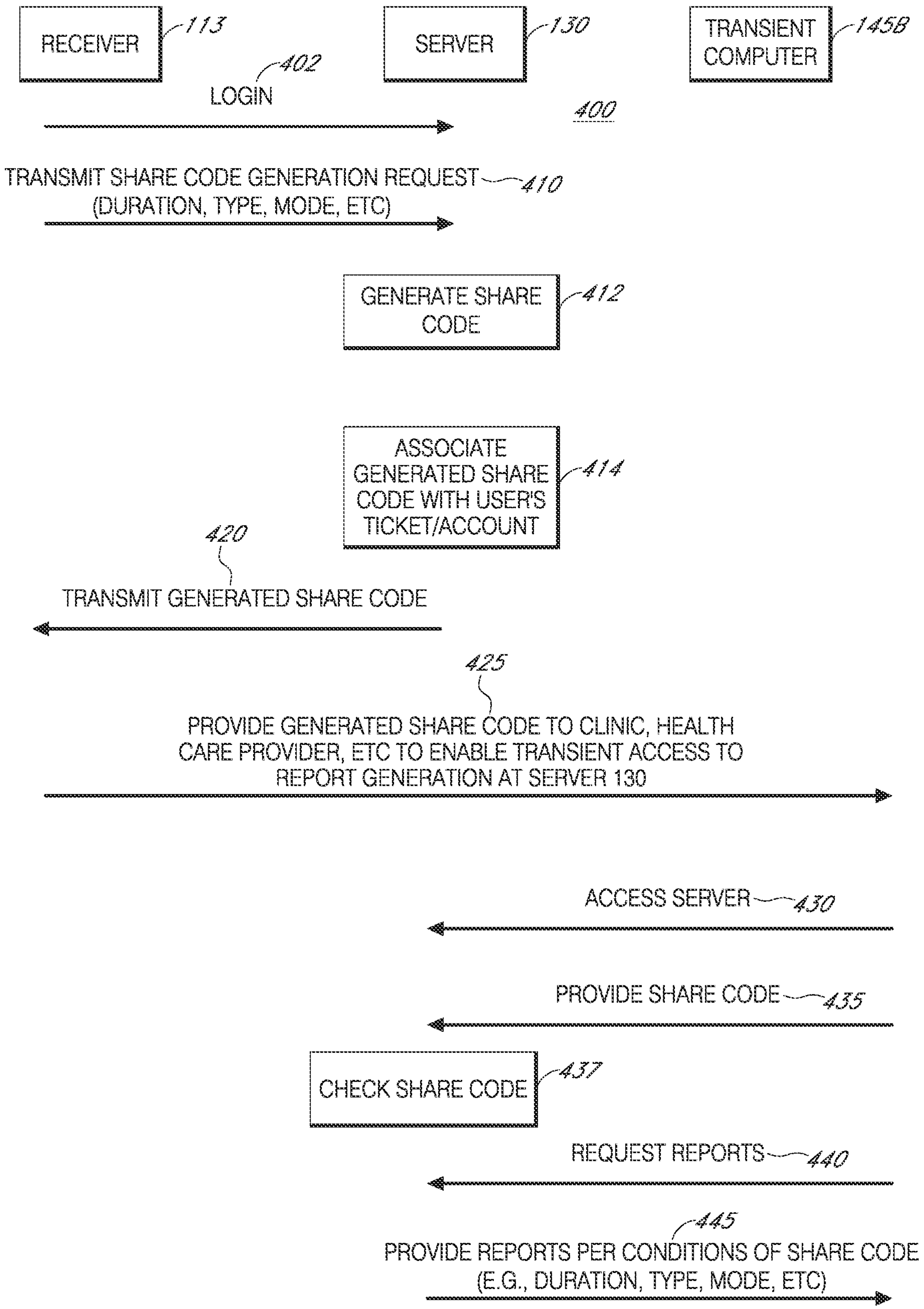
FIG. 4A depicts an example process for generating a share code, in accordance with some example embodiments.

FIG. 4A depicts an example process 400 for using a share code, in accordance with some example embodiments. The description of FIG. 4A also refers to FIG. 1.

At 402, a user of receiver, such as device 113 for example, may login to server 130 using for example a user name and password. Next, the receiver associated with a host patient (currently logged in) may transmit, at 410, a request to server 130 for a share code. For example, the device 113 may present a user interface view where a selection may be performed indicating that a share code mode (referred to above as the third sharing mode). This selection may trigger the transmission, at 410, of the request. The request transmitted at 410 may be transmitted in a wireless and/or a wired manner via network 120 to secure server 130.

In some example embodiments, the share code selection may include a selection of one or more options. For example, the option selection may include a duration for the share code. The duration may define a time during which the share code is valid, and, as such, the secure server can provide CGM data and/or reports so long as the duration has not expired. The duration option may be selected as 5, minutes, 10 minutes, 30 minutes, 1 hour, 2 hours, 3 hours, 24 hours, 2 days, 3 days, 1 week, 1 month, 2 months, 3 months, or any other duration.

In some example embodiments, the options selection may be type of reports. In some example embodiments, the options selection may include a selection of mode, such as report generation mode access, calibration mode access, and the like.

For the patient that is registered to the device 113 and logged in, the secure server may generate, at 412, a share code. For example, the share code may comprise a unique sequence of numbers, letters, characters, and/or symbols, and/or combinations thereof. In some implementations, the share code may comprise a unique sequence of 8 numbers, 9 numbers, 10 numbers, 11 numbers, 12 numbers 13 numbers, and the like, although the sequence may have other lengths as well. Although the previous example refers to a sequence of numbers, the share code may comprise a sequence of characters, symbols, numbers, or combination thereof of any length.

Figure 4B:
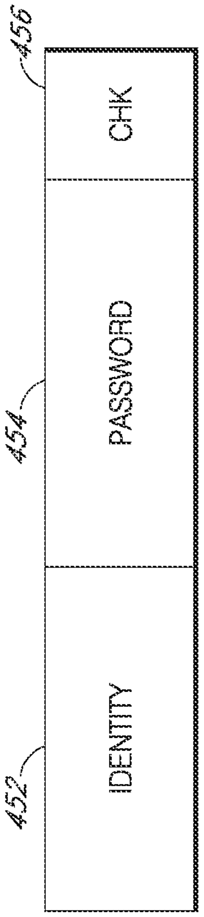
FIG. 4B depicts an example of a share code, in accordance with some example embodiments.

FIG. 4B depicts an example share code, in accordance with some example embodiments. In the example of FIG. 4B, the share code includes a checksum portion comprising one or more bits 456, a password portion comprising one or more bits 454, and/or an identity 452 comprising one or more bits. This three-layer share code may enable easier authentication by the secure server. For example, a quick check of the checksum may result in a denial of access (a server response indication access denied, for example). Although FIG. 4B depicts a certain format for the share code, the share code may take other forms as well.

The check sum may take a variety of forms. For example, the check sum may comprise a parity bit, a hash function, a check digit algorithm, a Damm algorithm, or the like.

In some example embodiments, an incorrect checksum may not be counted as a failed attempt, which might trigger an account lockout, for example. If the checksum is in error, the request may be denied as noted. However, if the password portion is incorrect as well, the server may keep track of the mistaken password portions. Moreover, if there are a certain quantity of fails attempts having an incorrect password portion, the secure server may lockout access to the server by the transient computer until some other verification is performed or a time out period lapses.

Referring again to FIG. 4A, the secure server may associate, at 414, the generated shared code with the patient's account (or ticket associated with the patient's login/account). With that association, the options, such as share code duration, mode, and type, may be recorded.

At 420, the generated share code may be transmitted to receiver 113. For example, the share code may be carried by a message, such as an email, SMS message, and any other type of message. When the generated share code is received, the share code may be extracted by the CGM application 135C, for example, and presented via a user interface at receiver 113.

At 425, the generated share code may be provided to another user at, for example, transient computer 145B. For example, the user of receiver 113 may send, via SMS, text, or by other mechanisms the generated share code to another user.

At 430, the other user may, via transient computer 145B, access the secure server via network 120. For example, the other user may access transient computer 145B/CGM application 135B, and then browse or otherwise access the secure server to provide the generated share code. To illustrate further, when the transient computer 145B/CGM application 135B access secure server 130, transient computer 145B/CGM application 135B may send a share code provided, via a user interface view, by the other user.

At 437, the secure server checks the share code. In some example embodiments, the share code includes a checksum, a password, and/or an identifier. When that is the case, the secure server may first check the checksum. If the password portion is incorrect, then the secure server rejects the share code and the requested access. Moreover, repeated password errors may count as failed attempts that can result in a lockout, as noted above.

If the secure server determines that the password portion is correct, then the secure server queries a database for the identifier portion, which is mapped to the patient's account or ticket. If the database includes the identifier portion, the identifier portion may be mapped to the patient's account or ticket. This mapping may indicate whether the share code is still valid. For example, the duration option may define a time over which the share code is valid. In some example embodiments, the database may set a timer based on the duration option. If the timer has not expired, access can be enabled. If the timer has expired, access will be denied. In some example embodiment, if the timer expires, the server's database may send and terminate access to the report generator to inform the report generator to stop providing CGM data and/or reports to the expired share code user at the transient computer.

Moreover, the mappings may include allowed modes and data types. When this is the case, the secure server may assess the allowed modes and types to determine whether to grant access.

If the share code has not expired and the access is granted, the secure server may allow report requests 440 to result in report generation being provided to the transient computer for presentation. If the share code has expired and the access is denied, the secure server will not allow reports to be provided and presented at the transient computer.

FIGS. 5-8 depict examples of reports that may be generated by secure server 130 and presented at a device or computer while in the first, second, or third sharing modes.

Figure 5:
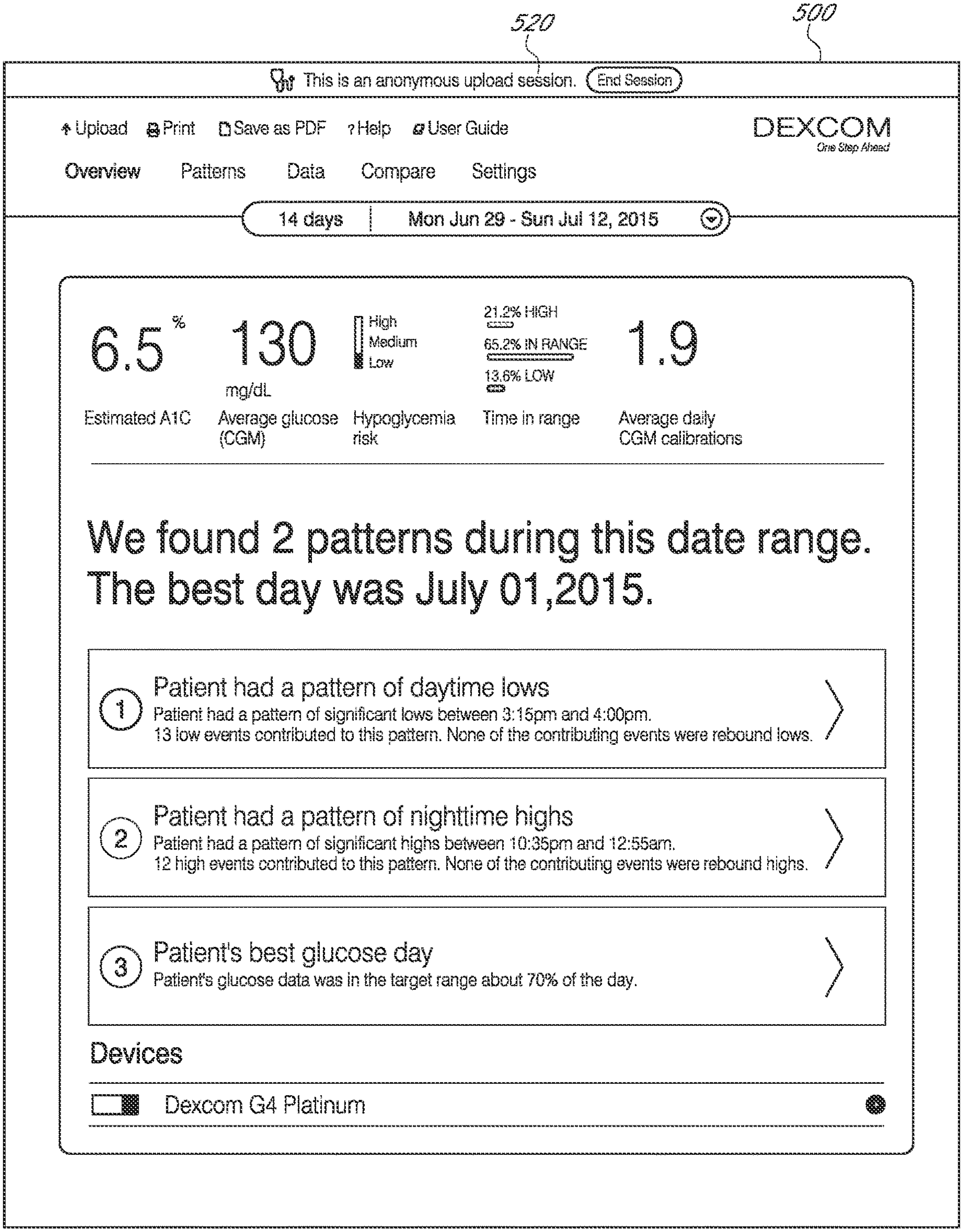
FIGS. 5 and 6 depict examples of reports generated, in accordance with some example embodiments.

FIG. 5 depicts an example of user interface view 500 of a report generated by the secure server. In the example report of FIG. 5, the user interface view 500 may be presented at a computer or other device. Moreover, the user interface view 500 may include an indication 520 that the report has been generated in the second sharing mode (or "anonymous upload session"). As can be seen by the report, there is no patient identifying information shown, but rather time range for the report, estimated A1C, average glucose level, time in range, hypoglycemia risk, and other information.

Figure 6:
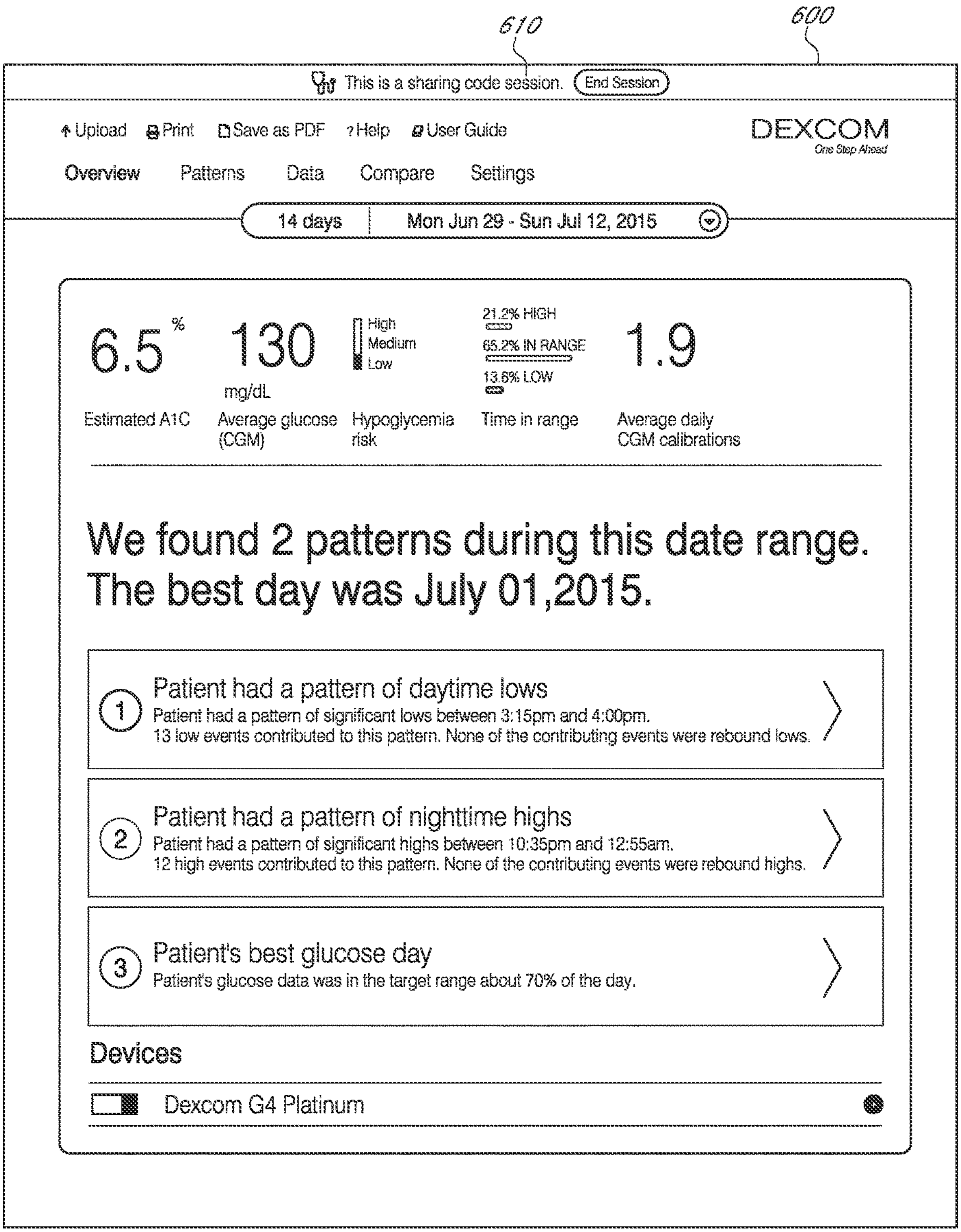

FIG. 6 depicts an example of a user interface view 600 of a report generated by the secure server. In the example report of FIG. 6, the user interface view 600 includes an indication 610 that the report has been generated in the third sharing mode (or "sharing code session"). In this example, the report is over a certain time range and includes estimated A1C, average glucose level, time in range, hypoglycemia risk, and other information.

Figure 7:
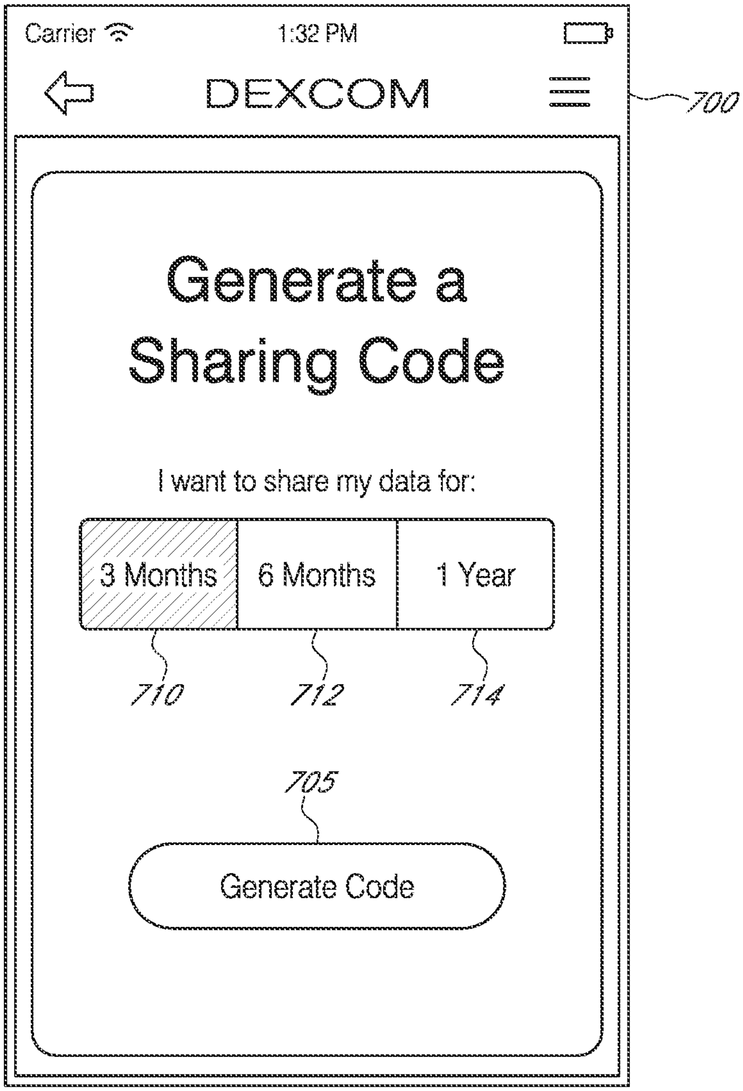
FIG. 7 depicts an example user interface view at which a share code and option can be selected and requested, in accordance with some example embodiments.

FIG. 7 depicts an example of a user interface view 700 presented at a device. The user interface view allows a request for the share code to be generated when the generate share code icon 705 is selected, and allows the selection of a duration option defining a time over which the share code is active (and thus enabling access to CGM data and/or report). In the example, the duration options include 3 months 710, 6 months 712, or 1 year 714. In other examples, the duration options can include 2 hours, 30 days, or 90 days, although other time periods may be used as well.

Figure 8:
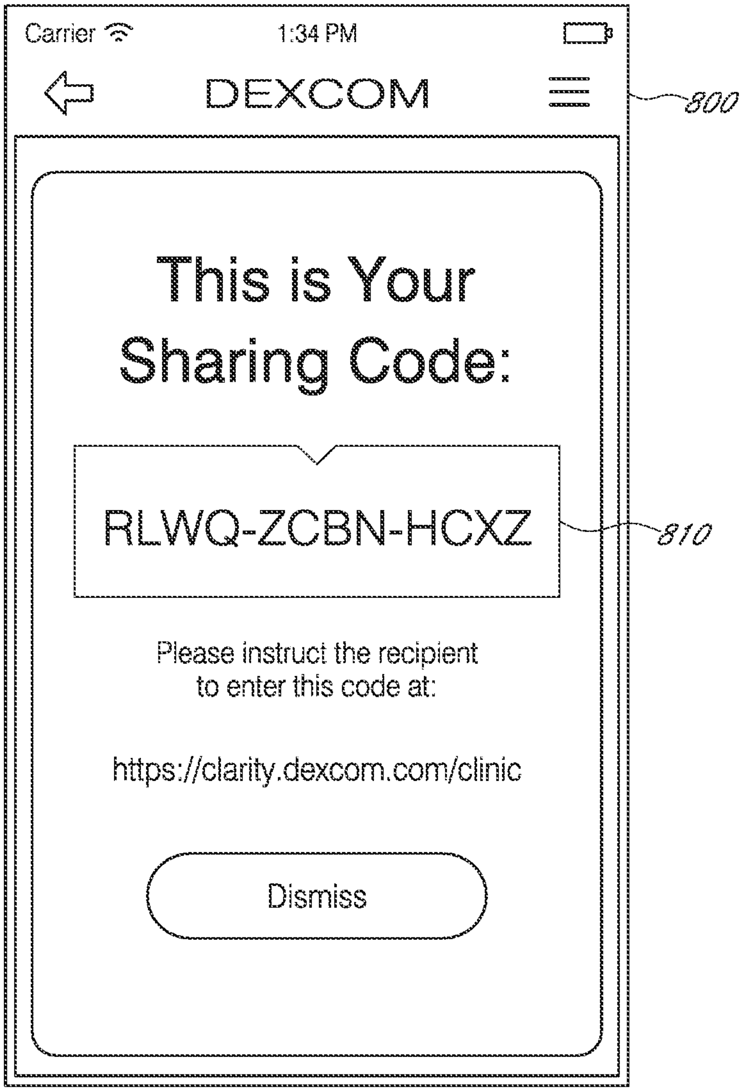
FIG. 8 depicts an example user interface view presenting a share code, in accordance with some example embodiments.

FIG. 8 depicts an example of a user interface view 800 presented at a device. The user interface view presents a share code 810. In this example, a host patient may provide another user with a share code. The other user may access, via an application such as a browser, the secure server at "clarity.dexcom.com/clinic." After accessing the secure server, the share code 810 may be entered as described above at 435.

EXAMPLES

The following examples are illustrative of several embodiments and implementations in accordance with the present technology. Other example embodiments and implementations of the present technology may be presented prior to the following listed examples, or after the following listed examples.

In some embodiments in accordance with the present technology (example 1), a method includes sending a message to a server, wherein the message includes a request for a share code to enable another user to access, via a first computer, analyte data obtained from a host-patient associated with a receiver and/or an analyte report for the host-patient associated with the receiver; receiving, in response to the sending, the share code generated by the server, wherein the share code comprises a checksum portion, a password portion, and an identifier portion indicative of the host-patient; generating a user interface view including the share code; and displaying the user interface view including the share code, in which the share code enables the other user to access, via the first computer, the analyte data and/or the analyte report.

Example 2 includes the method of example 1, further including providing, by the first computer including an application, the share code to the server.

Example 3 includes the method of example 2, in which the application comprises a downloaded application and/or a browser that accesses, via a wired connection and/or wireless connection, the server.

Example 4 includes the method of example 2, in which the providing comprises at least one of entering the share code at a webpage generated by the server; or sending to the server another message including the share code.

Example 5 includes the method of example 2, further including checking, by the server, the share code to determine whether an account associated with the host-patient indicates that the share code authorizes report generation at the first computer.

Example 6 includes the method of example 5, in which the checking further comprises checking the checksum portion of the share code; checking the password portion of the share code, when the checksum is valid; and verifying the identity portion of the share code by checking whether the identity portion maps to the account associated with the host-patient, when the checksum and password portion are valid.

Example 7 includes the method of example 6, in which the verifying further includes determining whether a lifetime for the share code has expired.

Example 8 includes the method of example 7, in which the lifetime is selected by the host-patient and/or configured as a default time.

Example 9 includes the method of example 5, further including generating, by the server, the analyte report, when the checking determines that report generation is authorized for presentation at the first computer.

Example 10 includes the method of example 1, further including triggering the sending of the request for the share code, when the host-patient accesses a share code request icon presented on webpage generated by the server.

Example 11 includes the method of example 1, in which a third sharing mode comprises enabling the other user to access, via the first computer, the analyte data obtained from host-patient associated with the receiver and/or the analyte report for the host-patient associated with the receiver.

Example 12 includes the method of example 1, further including uploading, when in a first sharing mode, to the server the analyte data obtained from the host-patient, wherein the analyte data comprises continuous glucose sensor data and patient identifying information identifying host-patient.

Example 13 includes the method of example 12, in which the uploading to the server further comprises transmitting the analyte data via at least one of a wired link, a cellular data link, a wireless local area network link, and/or a Bluetooth link.

Example 14 includes the method of example 12, in which the uploading is performed by the receiver configured to wirelessly receive at least the continuous glucose sensor data from a continuous glucose sensor affixed to the host-patient.

Example 15 includes the method of example 12, in which the uploading is via a remote computer.

Example 16 includes the method of example 12, in which the uploading is triggered when the receiver couples via at a wired connection and/or a wireless connection to the remote computer that is authenticated by the server.

Example 17 includes the method of example 16, in which the authentication comprises a login to an account associated with the host-patient.

Example 18 includes the method of example 12, further including generating, for presentation at the remote computer, the analyte report, wherein the analyte report comprises the analyte data and patient identifying information identifying the host-patient.

Example 19 includes the method of example 1, further including uploading, when in a second sharing mode, to the server the analyte data obtained from the host-patient, wherein the analyte data includes continuous glucose sensor data and excludes patient identifying information identifying the host-patient.

Example 20 includes the method of example 19, in which the receiver excludes the patient identifying information by at least one of removing, masking, or encrypting the patient identifying information.

Example 21 includes the method of example 19, in which the uploading further comprises transmitting, by the receiver, the analyte data via at least one of a wired link, a cellular data link, a wireless local area network link, and/or a Bluetooth link.

Example 22 includes the method of example 19, in which the receiver wirelessly receives the analyte data from a continuous glucose sensor affixed to the host-patient.

Example 23 includes the method of example 19, in which the uploading is via the first computer comprising a transient computer, wherein the transient computer is not logged into an account associated with host-patient.

Example 24 includes the method of example 23, in which the uploading is triggered by at least one of coupling the receiver via at a wired connection and/or wireless connection to the transient computer; and receiving an indication of a selection of an icon on a webpage, in which the icon represents the second sharing mode, wherein the second sharing mode enables the other user to access the analyte data obtained from the host-patient associated with the receiver and/or the analyte report for the host-patient associated with the receiver, in which the second sharing mode inhibits sharing of the patient identifying information identifying the host-patient.

Example 25 includes the method of example 19, further including triggering, when in the second sharing mode, the uploading by sending a second sharing mode upload message from the server to the transient computer and/or the receiver.

Example 26 includes the method of example 25, further including generating the analyte report for presentation at the transient computer, when the second sharing mode upload message is received.

In some embodiments in accordance with the present technology (example 27), a system includes at least one processor; and at least one memory including code which, when executed by the at least one processor, provides operations including sending a message to a server, wherein the message includes a request for a share code to enable another user to access, via a first computer, analyte data obtained from a host-patient associated with a receiver and/or an analyte report for the host-patient associated with the receiver; receiving, in response to the sending, the share code generated by the server, wherein the share code comprises a checksum portion, a password portion, and an identifier portion indicative of the host-patient; generating a user interface view including the share code; and displaying the user interface view including the share code, wherein the share code enables the other user to access, via the first computer, the analyte data and/or the analyte report.

Example 28 includes the system of example 27, further including providing, by the first computer including an application, the share code to the server.

Example 29 includes the system of example 28, in which the application comprises a downloaded application and/or a browser that accesses, via a wired connection and/or wireless connection, the server.

Example 30 includes the system of example 28, in which the providing comprises at least one of entering the share code at a webpage generated by the server; or sending to the server another message including the share code.

Example 31 includes the system of example 28, further including checking, by the server, the share code to determine whether an account associated with the host-patient indicates that the share code authorizes report generation at the first computer.

Example 32 includes the system of example 31, in which the checking further includes checking the checksum portion of the share code; checking the password portion of the share code, when the checksum is valid; and verifying the identity portion of the share code by checking whether the identity portion maps to the account associated with the host-patient, when the checksum and password portion are valid.

Example 33 includes the system of example 32, in which the verifying further comprises determining whether a lifetime for the share code has expired.

Example 34 includes the system of example 33, in which the lifetime is selected by the host-patient and/or configured as a default time.

Example 35 includes the system of example 31, further including generating, by the server, the analyte report, when the checking determines that report generation is authorized for presentation at the first computer.

Example 36 includes the system of example 27, further including triggering the sending of the request for the share code, when the host-patient accesses a share code request icon presented on webpage generated by the server.

Example 37 includes the system of example 27, in which a third sharing mode comprises enabling the other user to access, via the first computer, the analyte data obtained from host-patient associated with the receiver and/or the analyte report for the host-patient associated with the receiver.

Example 38 includes the system of example 27, further including uploading, when in a first sharing mode, to the server the analyte data obtained from the host-patient, wherein the analyte data comprises continuous glucose sensor data and patient identifying information identifying host-patient.

Example 39 includes the system of example 38, in which the uploading to the server further comprises transmitting the analyte data via at least one of a wired link, a cellular data link, a wireless local area network link, and/or a Bluetooth link.

Example 40 includes the system of example 38, in which the uploading is performed by the receiver configured to wirelessly receive at least the continuous glucose sensor data from a continuous glucose sensor affixed to the host-patient.

Example 41 includes the system of example 38, in which the uploading is via a remote computer.

Example 42 includes the system of example 38, in which the uploading is triggered when the receiver couples via at a wired connection and/or a wireless connection to the remote computer that is authenticated by the server.

Example 43 includes the system of example 42, in which the authentication comprises a login to an account associated with the host-patient.

Example 44 includes the system of example 38, further including generating, for presentation at the remote computer, the analyte report, in which the analyte report comprises the analyte data and patient identifying information identifying the host-patient.

Example 45 includes the system of example 27, further including uploading, when in a second sharing mode, to the server the analyte data obtained from the host-patient, in which the analyte data includes continuous glucose sensor data and excludes patient identifying information identifying the host-patient.

Example 46 includes the system of example 45, in which the receiver excludes the patient identifying information by at least one of removing, masking, or encrypting the patient identifying information.

Example 47 includes the system of example 45, in which the uploading further comprises transmitting, by the receiver, the analyte data via at least one of a wired link, a cellular data link, a wireless local area network link, and/or a Bluetooth link.

Example 48 includes the system of example 45, in which the receiver wirelessly receives the analyte data from a continuous glucose sensor affixed to the host-patient.

Example 49 includes the system of example 45, in which the uploading is via the first computer comprising a transient computer, wherein the transient computer is not logged into an account associated with host-patient.

Example 50 includes the system of example 49, in which the uploading is triggered by at least one of coupling the receiver via at a wired connection and/or wireless connection to the transient computer; and receiving an indication of a selection of an icon on a webpage, wherein the icon represents the second sharing mode, wherein the second sharing mode enables the other user to access the analyte data obtained from the host-patient associated with the receiver and/or the analyte report for the host-patient associated with the receiver, wherein the second sharing mode inhibits sharing of the patient identifying information identifying the host-patient.

Example 51 includes the system of example 45, further including triggering, when in the second sharing mode, the uploading by sending a second sharing mode upload message from the server to the transient computer and/or the receiver.

Example 52 includes the system of example 45, further including generating the analyte report for presentation at the transient computer, when the second sharing mode upload message is received.

In some embodiments in accordance with the present technology (example 53), a non-transitory computer readable storage medium including program code which when executed by at least one processor causes operations includes sending a message to a server, wherein the message includes a request for a share code to enable another user to access, via a first computer, analyte data obtained from a host-patient associated with a receiver and/or an analyte report for the host-patient associated with the receiver; receiving, in response to the sending, the share code generated by the server, wherein the share code comprises a checksum portion, a password portion, and an identifier portion indicative of the host-patient; generating a user interface view including the share code; and displaying the user interface view including the share code, wherein the share code enables the other user to access, via the first computer, the analyte data and/or the analyte report.

In some embodiments in accordance with the present technology (example 54), an apparatus includes means for sending a message to a server, wherein the message includes a request for a share code to enable another user to access, via a first computer, analyte data obtained from a host-patient associated with a receiver and/or an analyte report for the host-patient associated with the receiver; means for receiving, in response to the sending, the share code generated by the server, wherein the share code comprises a checksum portion, a password portion, and an identifier portion indicative of the host-patient; means for generating a user interface view including the share code; and means for displaying the user interface view including the share code, wherein the share code enables the other user to access, via the first computer, the analyte data and/or the analyte report.

In some embodiments in accordance with the present technology (example 55), a method includes generating, by a server, a first report including analyte data obtained from a host-patient associated with a receiver and excluding patient identifying information identifying host-patient, when in a first sharing mode; generating, by the server, a second report including the analyte data obtained from the host-patient associated with the receiver and including patient identifying information identifying the host-patient, when in a second sharing mode; and generating, by the server during a specified lifetime, a third report including the analyte data obtained from the host-patient associated with the receiver, when in a third sharing mode.

Example 56 includes the method of example 55, in which the first sharing mode includes triggering a data upload to the server to include the analyte data and exclude the patient identifying information identifying the host-patient.

Example 57 includes the method of example 55, in which the first sharing mode is triggered when the receiver providing the data is not registered with the server.

Example 58 includes the method of example 55, in which the first sharing mode is triggered when the receiver providing the data is not logged in and/or authenticated by the server.

Example 59 includes the method of example 55, in which the second sharing mode includes triggering a data upload to the server to include the analyte data and include the patient identifying information identifying the host-patient.

Example 60 includes the method of example 55, in which the second sharing mode is triggered when the receiver providing the data is registered with the server.

Example 61 includes the method of example 55, in which the second sharing mode is triggered when the receiver providing the data is not logged in and/or authenticated by the server.

Example 62 includes the method of example 55, wherein the third sharing mode includes providing a share code to enable sharing of the generated report during the specified lifetime.

Example 63 includes the method of example 62, in which the share code comprises a checksum portion, a password portion, and an identifier portion indicative of the host-patient Example 64 includes the method of example 55, in which the third sharing mode is triggered when a share code is received at the server.

Example 65 includes the method of example 55, further including sending at least one of the first report, the second report, and/or the third report.

Example 66 includes the method of example 55, further including sending to the receiver an indication regarding whether to include or exclude the patient identifying information.

In some embodiments in accordance with the present technology (example 67), a system includes at least one processor; and at least one memory including code which, when executed by the at least one processor, provides operations including generating, by the system, a first report including analyte data obtained from a host-patient associated with a receiver and excluding patient identifying information identifying host-patient, when in a first sharing mode; generating, by the system, a second report including the analyte data obtained from the host-patient associated with the receiver and including patient identifying information identifying the host-patient, when in a second sharing mode; and generating, by the system during a specified lifetime, a third report including the analyte data obtained from the host-patient associated with the receiver, when in a third sharing mode.

Example 68 includes the system of example 67, in which the first sharing mode includes triggering a data upload to the server to include the analyte data and exclude the patient identifying information identifying the host-patient.

Example 69 includes the system of example 67, in which the first sharing mode is triggered when the receiver providing the data is not registered with the system.

Example 70 includes the system of example 67, in which the first sharing mode is triggered when the receiver providing the data is not logged in and/or authenticated by the system.

Example 71 includes the system of example 67, wherein the second sharing mode includes triggering a data upload to the system to include the analyte data and include the patient identifying information identifying the host-patient.

Example 72 includes the system of example 67, in which the second sharing mode is triggered when the receiver providing the data is registered with the system.

Example 73 includes the system of example 67, in which the second sharing mode is triggered when the receiver providing the data is not logged in and/or authenticated by the system.

Example 74 includes the system of example 67, wherein the third sharing mode includes providing a share code to enable sharing of the generated report during the specified lifetime.

Example 75 includes the system of example 74, wherein the share code comprises a checksum portion, a password portion, and an identifier portion indicative of the host-patient.

Example 76 includes the system of example 67, wherein the third sharing mode is triggered when a share code is received at the system.

Example 77 includes the system of example 67, further including sending at least one of the first report, the second report, and/or the third report.

Example 78 includes the system of example 67, further including sending to the receiver an indication regarding whether to include or exclude the patient identifying information.

Example 79 includes the system of example 67, in which the system comprises at least one of a server or a secure server.

In some embodiments in accordance with the present technology (example 80), a non-transitory computer readable storage medium including program code which, when executed by at least one processor, causes operations including generating, by a server, a first report including analyte data obtained from a host-patient associated with a receiver and excluding patient identifying information identifying host-patient, when in a first sharing mode; generating, by the server, a second report including the analyte data obtained from the host-patient associated with the receiver and including patient identifying information identifying the host-patient, when in a second sharing mode; and generating, by the server during a specified lifetime, a third report including the analyte data obtained from the host-patient associated with the receiver, when in a third sharing mode.

In some embodiments in accordance with the present technology (example 81), an apparatus includes means for generating a first report including analyte data obtained from a host-patient associated with a receiver and excluding patient identifying information identifying host-patient, when in a first sharing mode; means for generating a second report including the analyte data obtained from the host-patient associated with the receiver and including patient identifying information identifying the host-patient, when in a second sharing mode; and means for generating, during a specified lifetime, a third report including the analyte data obtained from the host-patient associated with the receiver, when in a third sharing mode.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, audible feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

What is claimed is:

1. A system comprising:

a receiver coupled to a network;

a remote computer coupled to the network; and a server coupled to the network, the server comprising at least one processor and at least one memory including instructions which, when executed by the at least one processor, cause the processor to:

receive, from the receiver over the network, analyte data associated with a host;

receive, from the remote computer over the network, a request to access the analyte data;

determine a sharing mode based, at least in part, on whether the remote computer is a trusted computer;

in a first sharing mode:

generate a first report including the analyte data and information identifying the host, and send, to the remote computer over the network, the first report for presentation on a display of the remote computer;

in a second sharing mode:

generate a second report including the analyte data and excluding the information identifying the host, and send, to the remote computer over the network, the second report for presentation on the display of the remote computer; and in a third sharing mode:

generate, during a specified lifetime, a third report including the analyte data, and send, to the remote computer over the network, the third report for presentation on the display of the remote computer.

2. The system of claim 1, wherein:

the first sharing mode comprises triggering a data upload from the receiver to the server to include the analyte data and the information identifying the host; and the first sharing mode is triggered when the receiver is not registered with the system or when the receiver is not logged in and authenticated by the server.

3. The system of claim 1, wherein:

the second sharing mode comprises triggering a data upload from the receiver to the system to include the analyte data and exclude the information identifying the host; and the second sharing mode is triggered when the receiver is registered with the server or when the receiver is not logged in and authenticated by the server.

4. The system of claim 1, wherein:

the third sharing mode comprises providing a share code to enable sharing of the third report during the specified lifetime; and the third sharing mode is triggered when the share code is received at the server or when a user selection is received.

5. The system of claim 4, wherein the share code comprises a checksum portion, a password portion, and an identifier portion indicative of the host.

6. The system of claim 1, wherein the instructions further cause the processor to:

send, to the receiver over the network, an indication regarding whether to include or exclude the information identifying the host.

7. The system of claim 1, wherein the server is a secure server.

8. A method for a server, the method comprising:

receiving, from a receiver over a network, analyte data associated with a host;

receiving, from a remote computer over the network, a request to access the analyte data;

determining a sharing mode based, at least in part, on whether the remote computer is a trusted computer;

in a first sharing mode:

generating a first report including the analyte data and information identifying the host, and sending, to the remote computer over the network, the first report for presentation on a display of the remote computer;

in a second sharing mode:

generating a second report including the analyte data and excluding the information identifying the host, and sending, to the remote computer over the network, the second report for presentation on the display of the remote computer; and in a third sharing mode:

generating, during a specified lifetime, a third report including the analyte data, and sending, to the remote computer over the network, the third report for presentation on the display of the remote computer.

9. The method of claim 8, wherein:

the first sharing mode comprises triggering a data upload from the receiver to the server to include the analyte data and the information identifying the host; and the first sharing mode is triggered when the receiver is not registered with the server or when the receiver is not logged in and authenticated by the server.

10. The method of claim 8, wherein:

the second sharing mode comprises triggering a data upload from the receiver to the server to include the analyte data and exclude the information identifying the host; and the second sharing mode is triggered when the receiver is registered with the server or when the receiver is not logged in and authenticated by the server.

11. The method of claim 8, wherein:

the third sharing mode comprises providing a share code to enable sharing of the third report during the specified lifetime; and the third sharing mode is triggered when the share code is received at the server or when a user selection is received.

12. The method of claim 11, wherein the share code comprises a checksum portion, a password portion, and an identifier portion indicative of the host.

13. The method of claim 8, further comprising:

sending, to the receiver over the network, an indication regarding whether to include or exclude the information identifying the host.

14. A system, comprising:

a server comprising a processor and a memory storing instructions executable by the processor, the instructions causing the processor to:

receive, from a receiver over a network, analyte data associated with a host;

receive, from a remote computer over the network, a request to access the analyte data;

determine a sharing mode based, at least in part, on whether the remote computer is a trusted computer;

in a first sharing mode:

generate a first report including the analyte data and information identifying the host, and send, to the remote computer over the network, the first report for presentation on a display of the remote computer;

in a second sharing mode:

generate a second report including the analyte data and excluding the information identifying the host, and send, to the remote computer over the network, the second report for presentation on the display of the remote computer; and in a third sharing mode:

generate during a specified lifetime, a third report including the analyte data, and send, to the remote computer over the network, the third report for presentation on the display of the remote computer.

15. The system of claim 14, wherein:

the first sharing mode comprises triggering a data upload from the receiver to the server to include the analyte data and the information identifying the host; and the first sharing mode is triggered when the receiver is not registered with the system or when the receiver is not logged in and authenticated by the server.

16. The system of claim 14, wherein:

the second sharing mode comprises triggering a data upload from the receiver to the system to include the analyte data and exclude the information identifying the host; and the second sharing mode is triggered when the receiver is registered with the server or when the receiver is not logged in and authenticated by the server.

17. The system of claim 14, wherein:

the third sharing mode comprises providing a share code to enable sharing of the third report during the specified lifetime; and the third sharing mode is triggered when the share code is received at the server or when a user selection is received.

18. The system of claim 17, wherein the share code comprises a checksum portion, a password portion, and an identifier portion indicative of the host.

19. The system of claim 14, wherein the instructions further cause the processor to:

send, to the receiver over the network, an indication regarding whether to include or exclude the information identifying the host.

20. The system of claim 14, wherein the server is a secure server.

* * * * *